United States Patent [19]

Mayo et al.

[11] Patent Number: 4,770,746
[45] Date of Patent: Sep. 13, 1988

[54] SPINNING BAND FRACTIONATING COLUMN

[75] Inventors: Dana W. Mayo, Brunswick, Me.; Ronald M. Pike, Pelham; Robert J. Hinkle, Hampton, both of N.H.

[73] Assignee: Microscale Organic Laboratory Corporation, New Castle, N.H.

[21] Appl. No.: 518

[22] Filed: Jan. 5, 1987

[51] Int. Cl.$^4$ .............................................. B01D 3/10
[52] U.S. Cl. .................................. 202/153; 202/161; 202/205; 202/237; 202/238; 202/267.1; 203/86; 203/91; 203/DIG. 2; 159/DIG. 7; 159/DIG. 16
[58] Field of Search ................... 202/161, 153, 267 R, 202/205, 237, 238, 189, 185.1; 203/DIG. 2, 86, 91, 98; 159/DIG. 7, DIG. 16

[56] References Cited

U.S. PATENT DOCUMENTS

| | | | |
|---|---|---|---|
| 2,251,185 | 7/1941 | Carter et al. | 202/161 |
| 2,383,377 | 8/1945 | Evans et al. | 202/190 |
| 2,400,021 | 5/1946 | Podbielniak | 202/153 |
| 2,427,142 | 9/1947 | Hornbacher et al. | 202/161 |
| 2,518,758 | 8/1950 | Cook | 203/DIG. 2 |
| 2,537,942 | 1/1951 | Martin | 202/189 |
| 2,538,957 | 1/1951 | Askevold et al. | 202/161 |
| 2,601,971 | 7/1952 | Todd | 202/161 |
| 2,608,528 | 8/1952 | Piros et al. | 202/161 |
| 2,609,335 | 9/1952 | Hickman | 202/153 |
| 2,701,789 | 2/1955 | White | 202/161 |
| 2,712,520 | 7/1955 | Nester | 203/DIG. 2 |
| 2,764,534 | 9/1956 | Nerheim | 202/153 |
| 2,783,401 | 2/1957 | Foster et al. | 202/153 |
| 3,002,897 | 10/1961 | Kirkland et al. | 202/190 |
| 3,080,303 | 3/1963 | Nerheim | 202/161 |

OTHER PUBLICATIONS

Perkin-Elmer, Model 131T, "A Compact, Complete 30-Plate Teflon Spinning Band Distillation Unit, Mayo et al., Microscale Organic Laboratory", John Wileys & Sons, 1986, p. 46.

Stinson, Stephen, "New Instrumental Techniques Debut at Pittsburgh Conference", Chem. Engineering News, Mar. 30, 1987, pp. 20 and 21.

*Primary Examiner*—David L. Lacey
*Assistant Examiner*—V. Manoharan
*Attorney, Agent, or Firm*—Thomas N. Tarrant

[57] ABSTRACT

Spinning band fractionating column apparatus is disclosed having a spinning band formed with a magnet embedded in its bottom end in the manner of a magnetic stirring vane for rotation by a rotating external magnetic field at the bottom of the apparatus. Reflux is controlled by an angled drip edge on a rotatable condenser column that passes a portion of dripped condensate to a collecting spout with the portion varying as rotation of the condenser column brings the drip from said edge closer or further from center opposition with the spout.

4 Claims, 2 Drawing Sheets

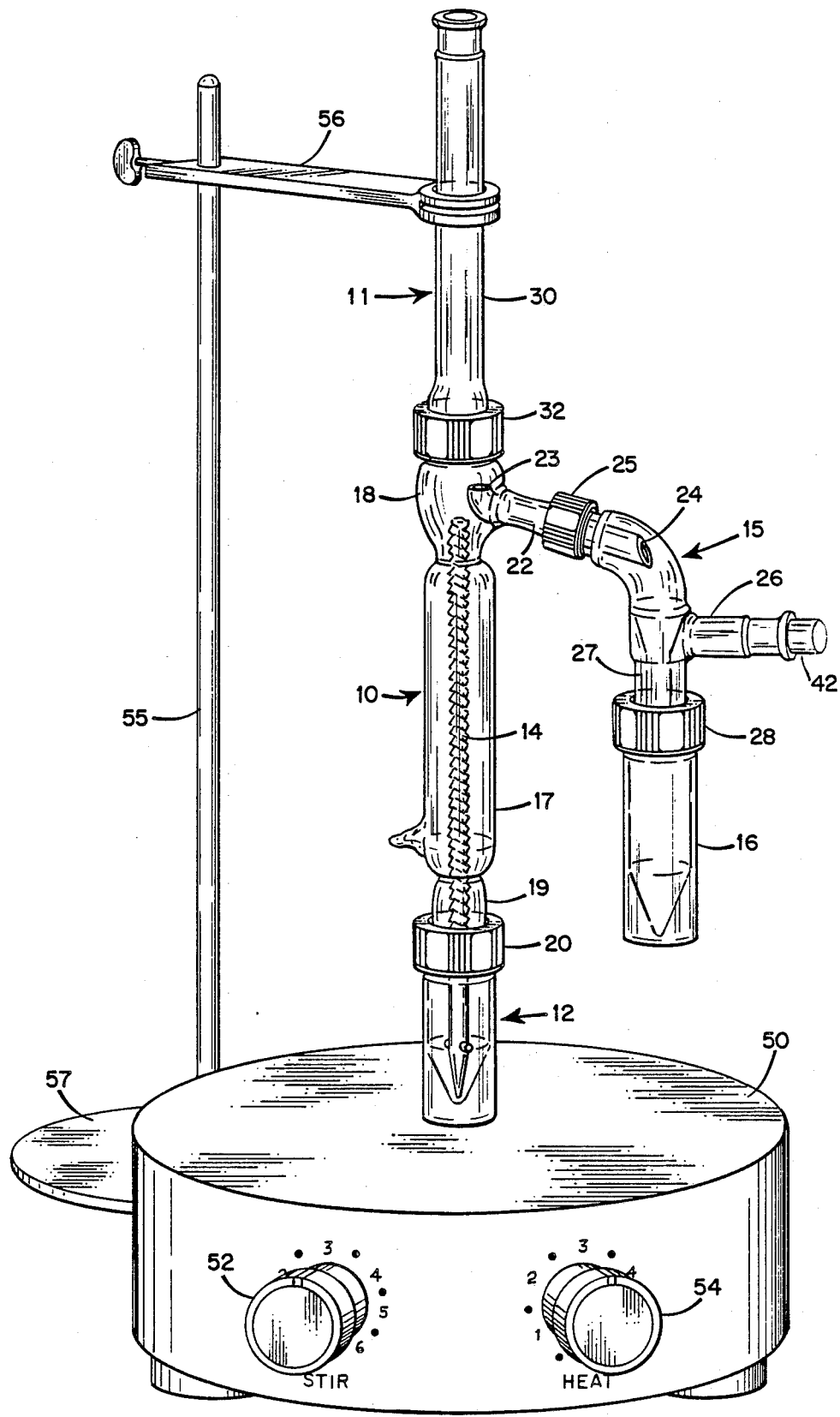

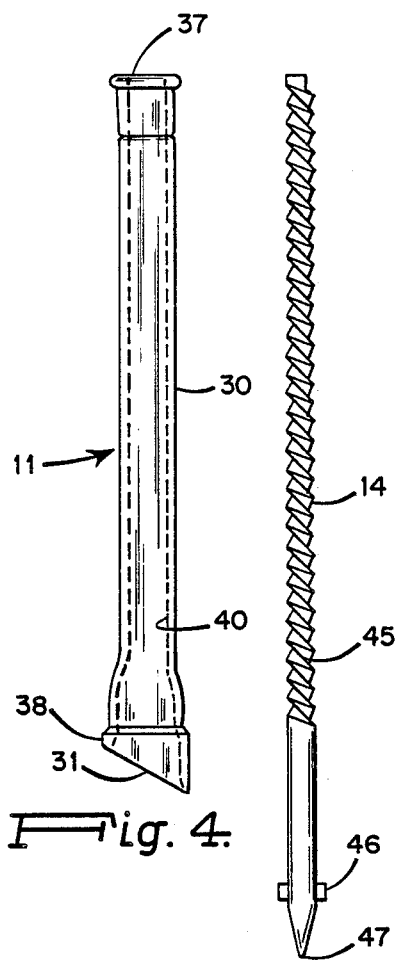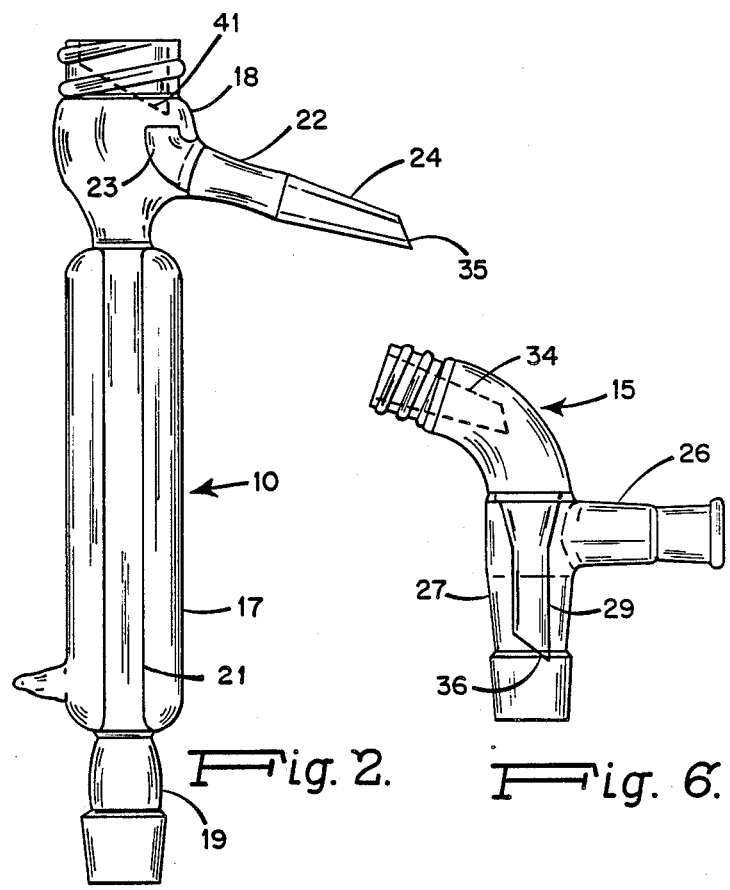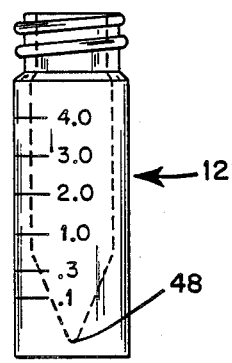

SPINNING BAND FRACTIONATING COLUMN

BACKGROUND OF THE INVENTION

1. Field of the Invention

The present invention relates to fractional distillation of chemical compositions and particularly to spinning band fractionating columns in which the band is caused to spin by an external rotating magnetic field.

2. Relation to the Prior Art

Effective separation by distillation techniques of close boiling (5°–10° C.) liquid mixtures which have volumes in the 0.5 to 5 ml. range currently involves the use of sophisticated and expensive equipment. Alternative routes utilizing preparative gas chromatographic instrumentation present an equally unattractive investment.

In 1938 the spinning band column was introduced for increasing fractionating efficiency. The first spinning band columns used directly coupled motors to rotate the band. In fractionating at below atmospheric pressure, leakage at the seals required for the direct coupling was a problem. As disclosed in U.S. Pat. No. 2,783,401 to Foster et al., magnetic coupling to an overhead motor avoided the seal problem. The arrangement remained cumbersome and expensive.

The bands themselves have been made mostly of metal. Various configurations have included metal strips, helical configurations and various disc shapes. More recently plastic bands have come into common use. U.S. Pat. No. 3,372,095 to Nester, discloses a band made of a rod of polytetrafluoroethylene wrapped with a spiral member of the same material. By making the spacing between the spiral member and the inner surface of the column small, the band is prevented from wobbling.

The overhead drive motor and an upper bearing for the spinning band necessitated by the drive arrangement has kept the expense high.

The present invention provides a novel low cost microdistillation column devoid of stopcocks and utilizing a plastic spinning band. The column achieves height equivalent/theoretical plate values approaching 0.5 cm/plate within 90 minutes of boilup.

The band utilizes a bottom magnetic drive system located in the distillation pot (still). Drive power is provided by conventional magnetic stirring plates. Thus, this system offers for the first time a very inexpensive distillation route to the separation of small quantities of low boiling liquid mixtures.

SUMMARY OF THE INVENTION

The present invention provides a spinning band fractionating column in which a magnetic material is incorporated in the bottom end of the band so that, when the column apparatus is placed on a conventional laboratory magnetic stirring plate, the band is caused to spin by the rotating field from the plate. A feature of the invention is a selfsupporting integral polymeric band pointed at the bottom end to provide its own needle bearing. A further feature is an angled drip-edge at the bottom of the condensing column which operated in conjunction with an outlet collecting spout to control reflux by rotation of the condensing column.

Further features of the invention will become apparent upon reading the following description together with the Drawing.

BRIEF DESCRIPTION OF THE DRAWING

FIG. 1 is an orthogonal projection of the inventive column.

FIG. 2 is a front elevation of the column portion of the assembly of FIG. 1.

FIG. 3 is a front elevation of the spinning band portion of the assembly of FIG. 1.

FIG. 4 is a front elevation of the condenser portion of the assembly of FIG. 1.

FIG. 5 is a front elevation of the still portion of the assembly of FIG. 1.

FIG. 6 is a front elevation of the output portion of the assembly of FIG. 1.

DESCRIPTION OF THE PREFERRED EMBODIMENT

FIG. 1 depicts the assembled spinning band column of the invention. As with most spinning band columns, there is column 10, condenser 11 connected to the top of column 10 and still 12 connected to the bottom of column 10. Spinning band 14 is positioned inside column 10 resting in still 12. Output connector 15 connects column 10 to collecting vial 16.

FIGS. 2 through 6 give the details of FIG. 1. Column 10 is shown in FIG. 2 as glass tube 21 surrounded by vacuum wall 17. Vacuum wall 17 is an evacuated glass cylinder surrounding tube 21 for thermal insulation. Fused to the upper end of tube 21 is reflux control chamber 18 which expands out to over twice the diameter of tube 21. Fused to the lower end of tube 21 is coupling chamber 19 which terminates in an externally ground end for a glass-to-glass seal with still 12. Screw cap 20 (FIG. 1) is held to chamber 19 by an elastomeric ring (not shown) and can be screwed to the top of still 12 to effect a stronger seal.

Drip tube 22 is a glass tube fused to reflux control chamber 18. Collection spout 23 is a first end of tube 22 that extends into chamber 18 and is turned upward to catch condensate coming down from condenser 11. Drip spout 24 is a second end of tube 22 that extends into output connector 15. Tube 22 is ground to a taper at the beginning of drip spout 24 to make a glass-to-glass seal with output connector 15. Screw cap 25 (FIG. 1) is retained on tube 22 by an elastomeric ring (not shown) and may be screwed on to output connector 15 to effect a stronger connection.

Tube 22 is fused to chmber 18 so that it slopes at a downward angle sufficient to ensure flow of condensate. Output connector 15 starts with an elbow turn to provide a downward arm 27 parallel with column 10. Side arm 26 is provided to allow attachment of pressure control means. A low pressure source may be connected to arm 26 for operating the column at below atmospheric pressure as is a common requirement. Arm 27 is taper ground at its bottom end for a glass-to-glass seal with collecting vial 16 (FIG. 1). Screw cap 28 is retained on arm 27 by an elastomeric ring (not shown) and may be screwed to collecting vial 16 for a stronger connection. Drip spout 29 may be added inside arm 27 to reduce losses due to condensate collecting on the walls of arm 27.

Drip spout 29 acts as a funnel to guide the drip to the mouth of vial 16. Dashed outline 34 shows the preferred position of drip spout 24 in output connector 15. This places lip 35 of spout 24 over the center of spout 29. Most drip will thus pass directly down into vial 16 without touching any glass walls after leaving spout 24.

Condensate that touches the wall of spout 29 or vapor that condensates on the wall of spout 29 will be guided by angled lip 36 to drip off the lower end of lip 36 into vial 16.

Condenser 11 (FIG. 4) is glass tube 30 having open top end 37 and taper ground bottom end 38. End 38 is ground for a glass-to-glass seal with reflux chamber 18. Screw cap 32 (FIG. 1) is retained on tube 30 by an elastomeric ring (not shown) and may be screwed onto chamber 18 to effect a stronger connection. End 38 terminates with angled lip 31. Lip 31 has an angle of substantially 20°, but the angle is not critical so long as it is sufficient to carry condensate running down tube 30 to the lowest point of lip 31 before it drips off. The inside of lip 31 is also beveled as indicated by dashed line 40 indicating the inner surface of tube 30.

Dashed line 41 in chamber 18 (FIG. 2) shows the position of lip 31 inside chamber 18 as it would be with condenser 11 assembled to column 10. This position can be changed by rotation of condenser 11. The particular position illustrated by dashed line 41 provides the minimum reflux. All or nearly all the condensate formed in condenser 11 is carried by lip 31 to drip directly into collecting spout 23. As the lowest point of lip 31 is rotated away from being centered over spout 23, the reflux is increased. Thus reflux is controlled in a simple fashion without the need of complex control valves.

With no drive mechanism extending through condenser 11, condenser 11 provides a ready receptacle for a monitoring thermometer. Such a thermometer preferably has its bulb suspended in reflux control chamber 18. This is easily accomplished by placing an elastomeric ring (not shown) tightly around a thermometer (not shown) at a location that suspends the thermometer from end 37. The elastomeric ring then also acts as a seal at end 37.

Both end 37 and side arm 26 can be blocked by stoppers or other means. In FIG. 1, stopper 42 is illustrated blocking arm Band 14, shown in FIG. 3, is integrally molded from polytetrafluoroethylene. Other plastic resins or nonmagnetic metals can be used, but the particular choice is made due to its low contact friction and inertness to most chemicals. Helical groove 45 is formed in the upper portion of band 14 so that it extends over the part of the band that will spin in column 10.

Small bar magnet 46 is molded into band 14 proximate bottom end 47. Bottom end 47 is formed in a point to act as a needle bearing resting on conical bottom 48 of still 12. The size of magnet 46 and its proximity to tip 47 is limited by the conical construction in still 12. Magnet 46 is proximate end 47 in the sense that it immediately follows end 47 to the extent permitted by the shape of the still in which band 14 is to be used.

Band 14 should have as large a diameter as can freely enter and rotate inside column 10. A band having a diameter of 5 mm has been used successfully in a column having an internal bore of 5.029 mm. The center-to-center position of magnet 46 was 12 mm from point 47. Magnet 46 was 7 mm in length and was molded into band 14 perpendicular to the band.

Both alnico 5 and alnico 8 magnet materials have been used to make magnet 46 and it is merely the conventional magnet used in magnetic stirring vanes commonly used with magnetic stirrers. In fact the present spinning band is made like a magnetic stirrer with the shape of the spinning band as described and illustrated herein instead of the short triangular shape of the stirring vane. The same magnet structure is embedded in the same way.

As shown in FIG. 1, The apparatus of the invention is used by positioning it on magnetic stirring plate 50. Laboratory stand 55 supports the fractionating column assembly by arm 56. Stand 55 has support base 57. Still 12 is shown resting directly on stirring plate 50, but is more usually positioned in a container having an amount of sand surrounding still 12 for heat distribution. Band 14 spins by the magnetic influence through both containers just as the conventional stirring vanes operate under the same circumstances.

Control 52 on plate 50 controls the speed of the rotating magnetic field and control 54 controls heat. Magnetic stirring plate 50 preferrably has a stirring rate up to 1000 rpm or higher and such plates are readily available. Examples are Corning Hot Plate Stirrer, Model PC-351 which operates at 250 to 1000 rpm and is available from Corning Glass Works, Houghton Park, Corning, NY 14830 and Fisher stirrer Model 3102 which operates up to 1500 rpm and is available from Fisher Scientific Co., 203 Fisher Bldg., Pittsburg, PA 15219.

In operation, the apparatus, assembled as in FIG. 1, is placed on a heated magnetic stirring plate. The magnetic field in the plate is rotated at the desired spin speed of the band. 1000 rpm is a common preferred speed of rotation. The plate heats the still to the desired temperature while providing the desired spin.

Examples of the performance characteristics of the bottom-driven spinning bnd fractionating column follow:

EXAMPLE 1. Twenty degree boiling pair: 2-methylpentane (60.5° C.) and cyclohexane (80.5° C.).

Volume: 1.5 mL/1.5 mL; Boilup Time 68 minutes.

Analysis: high resolution capillary gas chromatograph; fused quartz with SE30 stationary phase; isothermal rt 33° C.

| FRACTION # | 2-METHYL-PENTANE | CYCLO-HEXANE | TIME |
|---|---|---|---|
| 1 | 99.428 | 0.573 | 68 min. |
| Head Temp: 59.5° C. | 99.426 | 0.575 | |
| Volume: 0.3 mL. | 99.436 | 0.565 | |
| Ave. | 99.4 | 0.6 | |
| 2 | 99.088 | 0.912 | 50 min. |
| Head Temp: 60.0° C. | 99.042 | 0.958 | |
| Volume: 0.5 mL. | 99.062 | 0.938 | |
| Ave. | 99.1 | 0.9 | |
| 3 | 98.442 | 1.558 | 16 min. |
| Head Temp: 60.0° C. | 98.458 | 1.542 | |
| Volume: 0.20 mL. | 98.482 | 1.518 | |
| Ave. | 98.5 | 1.5 | |
| 4 | 74.447 | 25.554 | 56 min. |
| Head Temp: 60-80° C. | 74.315 | 25.685. | |
| Volume: 0.50 mL. | 74.473 | 25.527 | |
| Ave. | 74.4 | 25.6 | |
| 5 | 2.299 | 97.701 | 3 min. |
| Head Temp: 80° C. | 2.312 | 97.688 | |
| Volume: 0.80 mL. | 2.296 | 97.704 | |
| Ave. | 2.3 | 97.7 | |
| 6 | 0.236 | 99.764 | 2 min. |
| Head Temp: 80° C. | 0.220 | 99.780 | |
| Volume: 0.50 mL. | 0.236 | 99.764 | |
| Ave. | 0.2 | 99.8 | |
| 7 | 0.217 | 99.783 | 0 min. |
| Pot Residue = | 0.325 | 99.675 | |
| Holdup | 0.218 | 99.782 | |
| Volume: 0.20 mL. | | | |
| Ave. | 0.2 | 99.8 | |

Total Time: 195 min. (3.25 hrs.)
TOTAL recovered 2-Methylpentane = 1.4 mL.

| | |
|---|---|
| -continued | |
| TOTAL recovered Cyclohexane = 1.3 mL. | |

Recovered 66% of the 2-Methylpentane with 99%+ purity.

Recovered 80% of the Cyclohexane with 98%+ purity.

Based on data obtained from Fraction #1:

Column performance=8.5 plates.

EXAMPLE 2. Seven degree boiling pair: 2-methylpentane (60.5° C.) and hexane (68° C.).

Volume: 1.0 mL and 1.0 mL; Boilup time: 170 minutes.

Analysis: high resolution capillary gas chromatograph; fused quartz with SE30 stationary phase; isothermal rt. 28° C.

| FRACTION # | 2-METHYL-PENTANE | HEXANE | TIME |
|---|---|---|---|
| 1 | 95.215 | 4.785 | 170 min. |
| Head Temp: 59.5° C. | 95.145 | 4.855 | |
| Volume: 0.2 mL. | 95.183 | 4.817 | |
| Ave. | 95.2 | 4.8 | |
| 2 | 92.771 | 7.229 | 40 min. |
| Head Temp: 59.0° C. | 92.784 | 7.217 | |
| Volume: 0.3 mL. | 92.711 | 7.289 | |
| Ave. | 92.8 | 7.2 | |
| 3 | 88.843 | 11.157 | 45 min. |
| Head Temp: 59.5° C. | 88.580 | 11.420 | |
| Volume: 0.2 mL. | 88.536 | 11.464 | |
| Ave. | 88.7 | 11.3 | |
| 4 | 84.522 | 15.478 | 25 min. |
| Head Temp: 59.0° C. | 84.566 | 15.434 | |
| Volume: 0.1 mL. | 84.528 | 15.472 | |
| Ave. | 84.5 | 15.5 | |
| 5 | 53.437 | 46.563 | 65 min. |
| Head Temp: 65° C. | 53.403 | 46.597 | |
| Volume: 0.4 mL. | 53.358 | 46.642 | |
| Ave. | 53.4 | 46.6 | |
| 6 | 18.494 | 81.506 | 25 min. |
| Head Temp: 67° C. | 18.504 | 81.496 | |
| Volume: 0.2 mL. | 18.366 | 81.634 | |
| Ave. | 18.4 | 81.6 | |
| 7 | 4.718 | 95.282 | 20 min. |
| Head Temp: 68° C. | 4.676 | 95.324 | |
| Volume: 0.2 mL | 4.721 | 95.279 | |
| Ave. | 4.7 | 95.3 | |
| 8 | 0.961 | 99.039 | 0 min. |
| Pot fraction | 0.970 | 99.030 | |
| Volume: 0.2 mL. | 0.634 | 99.366 | |
| Ave. | 0.9 | 99.1 | |

Total Time: 390 min. (6.5 hrs)

TOTAL Recovered 2-Methylpentane = 1.0 mL.

TOTAL Recovered Hexane = 0.9 mL.

Recovered 50% of the 2-Methylpentane with 95+% purity.

Recovered 50% of the n-Hexane with 95+% purity.

Based on data obtained from Fraction #1:

Column Performance=11.2 plates.

While the invention has been described with reference to a specific embodiment, other configurations are contemplated as within the scope of the invention. For example, the rotating magnetic field can be provided by a stator surrounding still 12 rather than by a plate underneath still 12. Band 14 can be convoluted in other ways used in spinning bands rather than by a helix. Also the column can be made of other materials than glass and other conventional internal configurations may be used. Thus it is intended to cover the invention as set forth in the following claims.

We claim:

1. A bottom-driven spinning band fractionating system comprising:
   a. a still;
   b. a fractionating column mounted on top of said still;
   c. a reflux control chamber connected to the top of said fractionating column;
   d. a condensing column connected to the top of said reflux control chamber;
   e. a spinning band element mounted for rotation in said fractionating column, said spinning band element has a first end positioned in said still and a second end extending upward through said fractionating column terminating at said reflux control chamber short of said condensing column; and, a magnetic material mounted on said first end, whereby positioning said still on a magnetic stirring plate causes said spinning band element to rotate.

2. A bottom-driven spinning band fractionating system according to claim 1 wherein said spinning band element is formed of plastic resin material and said magnetic material is a bar magnet imbedded in said plastic resin.

3. A bottom-driven spinning band fractionating system according to claim 1 wherein said still has a conical internal bottom surface and said spinning band first end bears against said bottom surface as a rotational bearing point.

4. A bottom-driven spinning band fractionating system according to claim 1 wherein said spinning band second end has helical groove element formed from above said magnetic material.

* * * * *